US006860142B2

United States Patent
Seevers et al.

(10) Patent No.: US 6,860,142 B2
(45) Date of Patent: Mar. 1, 2005

(54) METHOD AND APPARATUS FOR MEASURING A VARIABLE IN A LUBRICANT/COOLANT SYSTEM

(75) Inventors: Stanley W. Seevers, Perrysburg, OH (US); Guy R. Hughes, Lawrenceburg, IN (US); Frank A. Robinson, Sylvania Township, OH (US)

(73) Assignee: Master Chemical Corporation, Perrysburg, OH (US)

( * ) Notice: Subject to any disclaimer, the term of this patent is extended or adjusted under 35 U.S.C. 154(b) by 0 days.

(21) Appl. No.: 10/366,978

(22) Filed: Feb. 14, 2003

(65) Prior Publication Data

US 2004/0159145 A1 Aug. 19, 2004

(51) Int. Cl.[7] ................................................ G01N 33/00
(52) U.S. Cl. .................... 73/61.59; 73/61.42; 73/53.05; 73/64.56; 73/61.41
(58) Field of Search ............................ 73/53.05, 61.41, 73/61.42, 61.59, 61.61, 64.56

(56) References Cited

U.S. PATENT DOCUMENTS

| 4,627,271 | A | * | 12/1986 | Abbott et al. .............. 73/54.06 |
| 4,935,863 | A | | 6/1990 | Calvas et al. |
| 4,992,380 | A | | 2/1991 | Moriarty et al. .............. 436/55 |
| 5,224,051 | A | | 6/1993 | Johnson ...................... 700/169 |
| 5,440,478 | A | | 8/1995 | Fisher et al. |
| 5,859,778 | A | | 1/1999 | Kuroda et al. |
| 5,946,215 | A | | 8/1999 | Mito |
| 6,144,923 | A | | 11/2000 | Grosse |
| 6,336,362 | B1 | | 1/2002 | Duenas |
| 6,546,785 | B1 | * | 4/2003 | Discenzo ................... 73/53.05 |

* cited by examiner

*Primary Examiner*—Daniel S. Larkin
(74) *Attorney, Agent, or Firm*—Brinks Hofer Gilson & Lione

(57) ABSTRACT

An automatic system for monitoring/controlling a variable of a machine or metalworking fluid system also achieves cleaning and optionally, a calibration check of the sensor of the variable. The system includes one or more sensors for variables such as pH, fluid concentration, conductivity, temperature and the like, a supply of a cleaning agent and associated valves and conduits for connecting the automatic system to a fluid to be measured. A cleaning cycle can be scheduled as necessary to clean and/or check calibration of the sensors and ensure accurate measurement of sensed variables. If desired, the data regarding the sensed variables may be utilized to perform corrective action in real time.

19 Claims, 4 Drawing Sheets

METHOD AND APPARATUS FOR MEASURING A VARIABLE IN A LUBRICANT/COOLANT SYSTEM

BACKGROUND OF THE INVENTION

The invention relates generally to a method and apparatus for measuring a variable in a fluid system and more particularly to a method and apparatus for measuring a fluid variable in a lubricant or coolant system and cleaning and undertaking a calibration check of the measurement device to ensure accurate measurement.

Most machine tools that remove metal, including automatic screw machines and computer controlled machining centers rely upon cooling and lubricating fluids applied to the machining site to improve tool life, enhance the surface finish of the machined region, increase cutting speeds and remove heat from the machining process to minimize distortion of the part and interference with or reduction of properties achieved by heat treatment.

Maintaining optimum concentrations and fluid characteristics of such cooling and lubricating fluids is desirable from the standpoints of maintaining optimum machining conditions, maximizing coolant and lubricant service life and therefore minimizing overall operating expense.

Numerous devices and methods have been developed to optimally use both cutting equipment and cooling and lubricating fluids. For example, U.S. Pat. No. 4,757,307 teaches a method of sensing the heat generated by a cutting tool to determine the condition of the tool.

U.S. Pat. No. 6,134,930 discloses a system wherein independent or distinct lubricating and cooling fluids are utilized to achieve distinct operational benefits.

Frequently, system operating conditions at the work site may be monitored and the information provided over land lines to a remote site where decisions regarding adjustment of fluid parameters are made and transmitted to the work site. Such a system is disclosed in U.S. Pat. No. 5,224,051.

In U.S. Pat. No. 6,336,362, a method and system for measuring and reporting the liquid level of tanks is taught. The system is particularly suited for detecting and reporting the level of liquid propane in industrial, commercial and residential tanks in order to prevent exhaustion of the gas supply at a particular site.

From the foregoing, it is apparent that monitoring and control systems relating to fluids, fluid quantity and fluid condition are diversified. Moreover, it is apparent that methods and apparatus addressing particular operational problems such as accurate measurement of a fluid variable such as pH, concentration, conductivity or temperature have not been fully developed. For example, many sensors are subject to fouling when exposed to coolants and lubricants and particularly so when the coolants and lubricants become contaminated. The present invention addresses and solves such problems.

BRIEF SUMMARY OF THE INVENTION

An automatic system for monitoring/controlling a variable of a machine or metalworking fluid system also achieves cleaning and optionally, a calibration check of the sensor of the variable. The system includes one or more sensors for variables such as pH, fluid concentration, conductivity, temperature and the like, a supply of a cleaning agent and associated valves and conduits for connecting the automatic system to a fluid to be measured. A cleaning cycle can be scheduled as necessary to clean and/or check calibration of the sensor or sensors and ensure accurate measurement of sensed variables. If desired the input to the system and output from the system may be connected to separate manifolds having corresponding pluralities of inputs and outputs. Also if desired, the data regarding the sensed variables may be utilized to perform corrective action in real time. Finally, sensed and operational data may be transmitted over telephone lines, the internet or other means to a remote site where monitoring and recording of the variables and operation may be undertaken.

Thus it is an object of the present invention to provide a method for monitoring at least one variable of a machine coolant or lubricant.

It is a further object of the present invention to provide an apparatus for monitoring at least one variable of a machine coolant or lubricant.

It is a still further object of the present invention to provide an apparatus and method for monitoring and controlling at least one variable of a machine coolant or lubricant.

It is a still further object of the present invention to provide a method and apparatus for cleaning and checking calibration of a fluid variable sensor.

It is a still further object of the present invention to provide a method and apparatus for cleaning and checking calibration of a fluid variable sensor for machine coolants and lubricants.

It is a still further object of the present invention to provide monitoring of at least one variable of machine coolants and lubricants and provide such information to a remotely located site.

Further objects and advantages of the present invention will become apparent by reference to the following description of the preferred embodiment and appended drawings wherein like reference numbers refer to the same component, element or feature.

DETAILED DESCRIPTION OF THE PREFERRED EMBODIMENT

Figure 1:
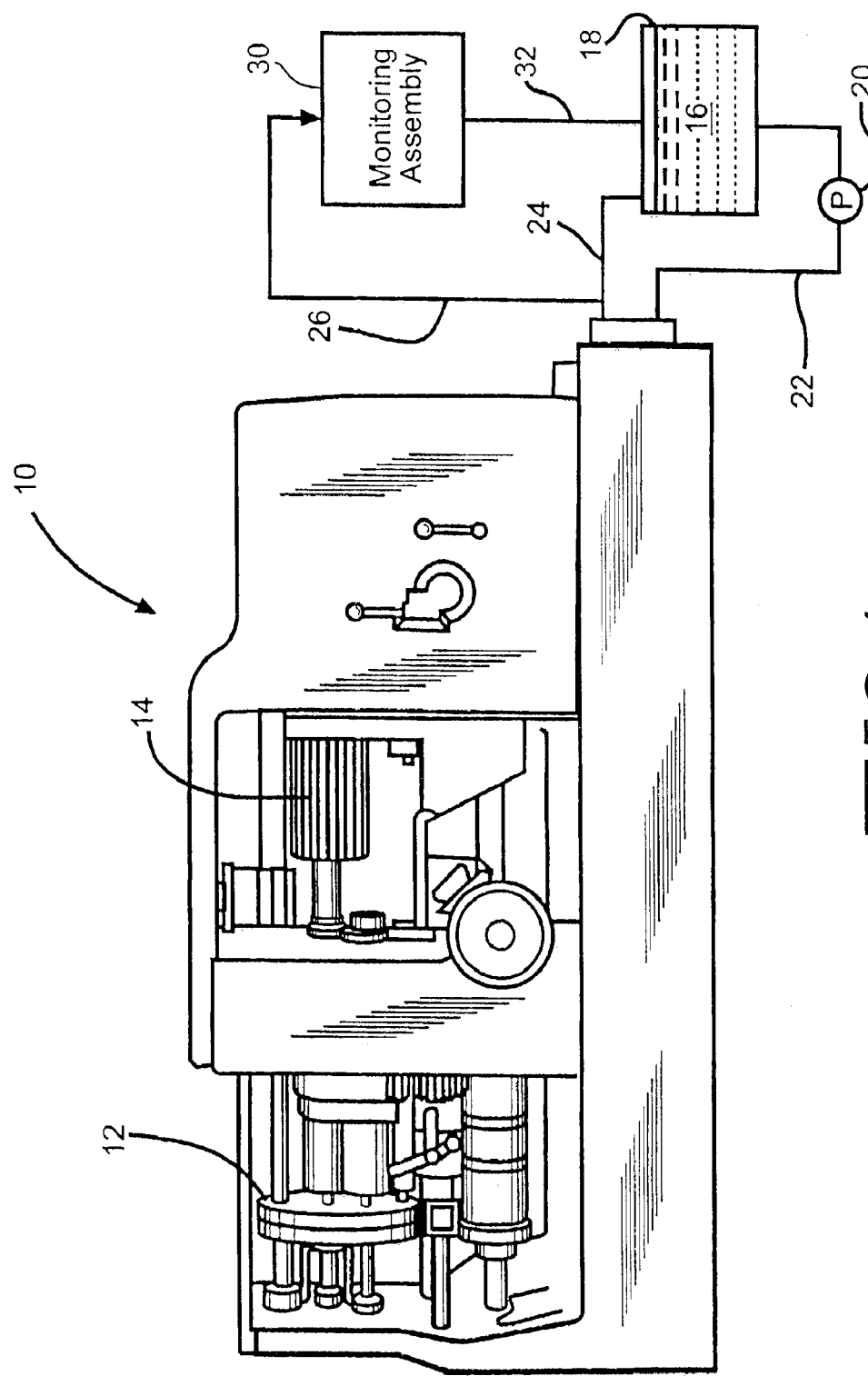
FIG. 1 is a diagrammatic view of an automatic screw machine which incorporates the present invention.

Referring now to FIG. 1, an automatic screw machine 10 incorporates various carriages 12 and magazines 14 for workpieces and tools which cooperate to manufacture various and sundry machine parts (not illustrated). It is to be understood that the automatic screw machine 10 is illustrative only and that the apparatus and method of the present invention may be and is intended to be utilized with such automatic screw machines 10, computer numerical controlled (CNC) devices and machining centers, lathes, grinders, milling machines, and all manner of equipment for cutting, forming, boring, milling, drilling and shaping of typically though not exclusively metal parts wherein the aforementioned processes are facilitated by application of cooling and/or lubricating fluids 16.

Such cooling and lubricating fluids 16 are typically stored in a sump 18 and may be supplied to the machine 10 under pressure by a pump 20 in a line 22. A return line 24 provides the cooling and lubricating fluid 16 directly to the sump 18. A second return and inlet or supply line 26 provides the cooling and lubricating fluid 16 to a coolant and lubricant monitoring assembly 30. Fluid 16 departing the coolant and lubricant monitoring assembly 30 is returned in an outlet line 32 to the sump 18 and thence recirculated.

Figure 2:
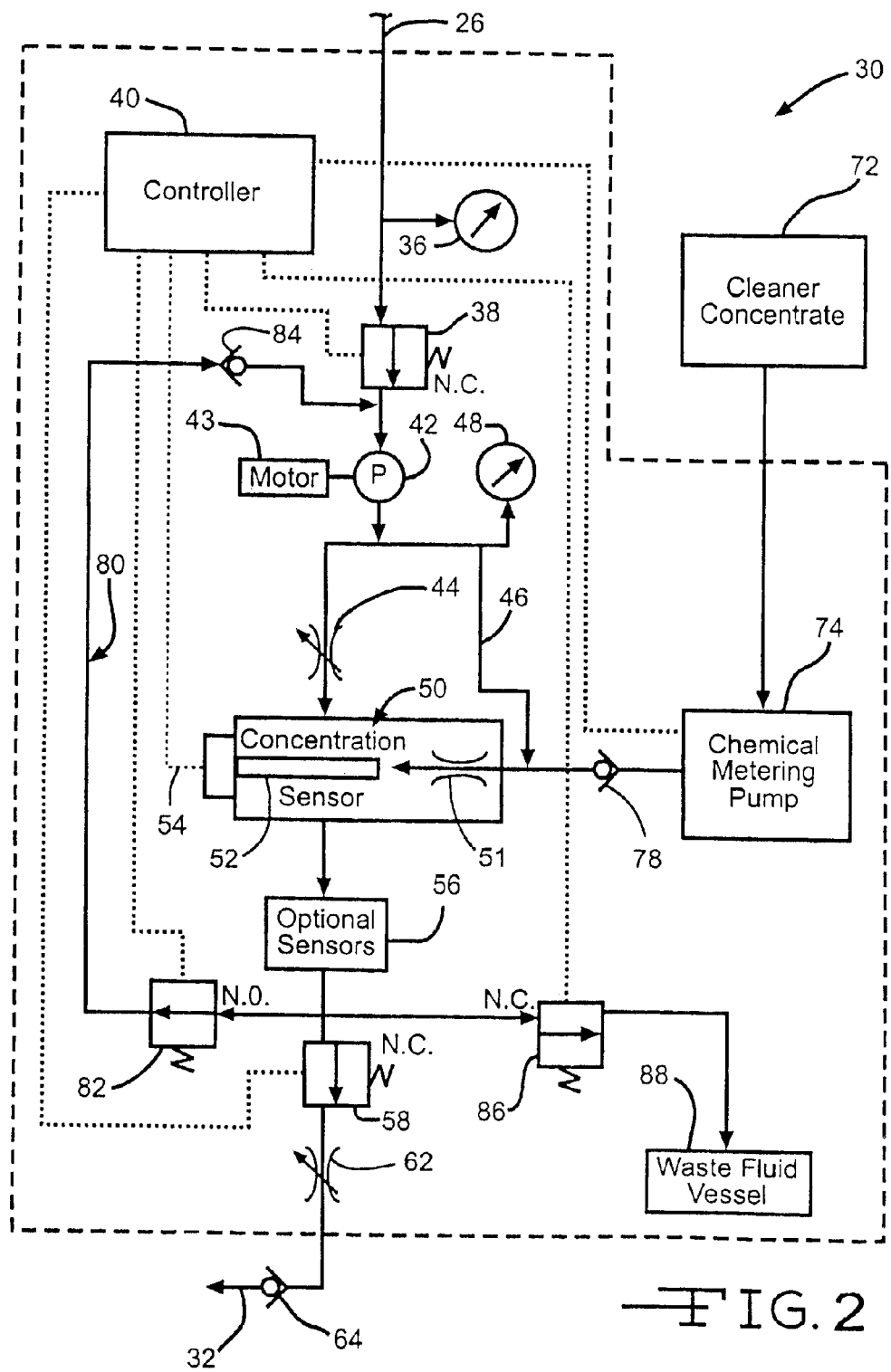
FIG. 2 is a block diagram of the components of an apparatus having a sensor for monitoring a variable of a machine coolant or lubricant and components for cleaning and providing a calibration check of such sensor according to the present invention.

Referring now to FIG. 2, the inlet or supply line 26 includes a first pressure gauge 36 which may be either a visually readable device such as a conventional Bourdon tube pressure gauge or may be a transducer which provides a signal to a remote location. The input or supply line 26 terminates in a normally closed, two position first solenoid valve 38 which may be opened or closed by a controller 40 to supply or inhibit a flow of the cooling or lubricating fluid 16 to the coolant and lubricant monitoring assembly 30. When the solenoid valve 38 is open, the cooling or lubricating fluid 16 is provided to a high pressure pump 42. The high pressure pump 42, which is driven by an electric motor 43, is capable of increasing the pressure of the fluid 16 to approximately 80 p.s.i. The actual operating pressure is adjusted by the restriction provided by a flow adjustment or restriction device 44. The restriction provided by the flow adjustment device 44 is increased to, increase pressure in a supply line 46 and is reduced to lower pressure therein, the preferred or optional operating pressure in the supply line 46 being a function of the type of cooling and lubricating fluid 16. A second pressure gauge 48 reads and indicates the pressure at the output of the high pressure pump 42 in the supply line 46. Once again, the second pressure gauge 48 may be a conventional (visual) gauge or a transducer providing a signal to a remote location.

As just described, the flow adjustment device 44 permits control of the pressure of the fluid 16 moving in the supply line 46. The pressurized cooling and lubricating fluid 16 is provided to a sensor assembly housing 50 through a small orifice 51 having a diameter on the order of 0.125 inches (3 mm). The fluid 16 which passes through the flow adjustment device 44 and thus not through the supply line 46 also flows to the sensor assembly housing 50. The sensor assembly housing 50 removably receives a refraction type concentration sensor 52 such as that available from several manufacturers including K-Patents, Naperville, Ill., AFAB Enterprises, Eustis, Fla., and Misco, Cleveland, Ohio. The concentration sensor 52 includes a face against which the flow of cooling and lubricating fluid 16 through the orifice 51 under an elevated pressure impinges. Output signals or data from the concentration sensor 52 are provided in output leads 54. Fluid 16 flows out from the sensor assembly housing 50 and may impinge upon, engage or pass through additional or optional sensors 56 such as a temperature sensor, a pH sensor, an electrical conductivity sensor, a turbidity sensor or other sensors providing information regarding diverse variables and the condition of the cooling or lubricating fluid 16.

The cooling and lubricating fluid 16 then travels to a normally closed second solenoid valve 58 which is activated and allows the measured cooling or lubricating fluid 16 to exit the monitoring assembly 30 through a second flow adjustment device 62. The second flow adjustment device 62 provides an adjustable restriction which ensures maintenance of suitable pressure within the monitoring assembly 30. The cooling or lubricating fluid 16 returns in the outlet line 32 to the sump 18 and associated equipment.

Described immediately above are the components of the coolant and lubricant monitoring assembly 30 relating to sensing of variables under routine operating conditions. These components constitute the path of the cooling or lubricating fluid 16 taken by a small percentage of the fluid 16 circulating in the system illustrated in FIG. 1 as it is bypassed through the monitoring assembly 30.

The coolant and lubricant monitoring assembly 30 also includes components adapted and intended to clean the concentration sensor 52 and any optional sensors 56. Thus, the monitoring assembly 30 includes a supply of a concentrated cleaner contained in a storage vessel 72 which is provided to a chemical metering pump 74. Preferably, the concentrated cleaner is and acts as a solvent for both the constituents and contaminants of the particular cooling and lubricating fluid 16 utilized such that its addition thereto facilitates softening, emulsification and removal of contaminants in the monitoring assembly 30.

The chemical metering pump 74 is activated for a preselected period of time by a timing feature in the controller 40. When commanded to operate by the controller 40, the chemical metering pump 74 operates for a preselected period of time to inject a controlled amount of the concentrated cleaner through a check valve 78 into the sensor assembly housing 50. The period of time is adjustable to accommodate and compensate for different cooling and lubricating fluids 16 and different concentrated cleaners.

Also associated with the cleaning function, is a bypass or cleaning loop 80 having a normally open third solenoid valve 82 which is operated by the controller 40 and a check valve 84 which is in fluid communication with the outlet of the third solenoid valve 82. A normally closed fourth solenoid valve 86 is also operated by the controller 40 and opens to dump fluid containing the concentrated cleaner or any other fluid within the coolant and lubricant monitoring assembly 30 to a waste vessel 88.

The cooling and lubricating fluid 16 then travels to a normally closed second solenoid valve 58 which is activated and allows the measured cooling or lubricating fluid 16 to exit the monitoring assembly 30 through a second flow adjustment device 62. The second flow adjustment device 62 provides an adjustable restriction which ensures maintenance of suitable pressure within the monitoring assembly 30. A check valve 64 ensures fluid flow only out of the monitoring assembly 30 in the line 32. The cooling or lubricating fluid 16 returns in the outlet line 32 to the sump 18 and associated equipment.

The first solenoid valve 38 is normally closed and when activated, receives cooling and lubricating fluid 16 in the line 26 from the external system. Simultaneously, the second normally closed solenoid valve 58 is also activated, providing an outlet for the incoming fluid 16. Pressure of the supplied cooling and lubricating fluid 16 is monitored by the first pressure gauge 36. With the normally open third solenoid valve 82 deactivated, fluid 16 readily flows through the bypass or cleaning loop 80 for a timed interval, flushing and displacing whatever fluid the bypass or cleaning loop 80 previously contained.

When the above flushing interval is complete, the normally open third solenoid valve 82 is activated and closes the bypass or cleaning loop 80. This action directs all incoming fluid 16 to the high pressure pump 42. The electric motor 43 of the high pressure pump 42 is activated to assist drawing in the cooling and lubricating fluid 16 to be measured and filling the various components of the coolant and lubricant monitoring assembly 30, flushing and displacing the previously contained fluid. The fluid 16 is thus provided to the sensor assembly housing 50, the concentration sensor 52 and other optional sensors 56 as wilt be readily appreciated. The normally closed second solenoid valve 58 remains activated and therefore open and permits fluid 16 to return to the main system through the flow adjustment device 62 and the return line 32.

When a measurement cycle is completed, the high pressure pump 42 is stopped and the controller 40 signals the chemical metering pump 74 to inject a measured amount of a concentrated cleaner into the monitoring assembly 30 through the check valve 78. The operating time of the metering pump 74 and thus the amount of concentrated cleaner injected is controlled by and can be adjusted by adjustment of software in the controller 40. Next, the normally closed first solenoid valve 38 is deactivated to close it, the normally closed second solenoid valve 58 is deactivated to close it and the normally open third solenoid valve 82 is deactivated to open it. The high pressure pump 42 is activated and the fluid 16 which now includes the concentrated cleaner is forced at high pressure onto the surfaces of the concentration sensor 52 to clean it and clean as well any optional sensors 56. The aforementioned bypass or cleaning loop 80 now functions as a fluid return path to the high pressure pump 42 so the cooling and lubricating fluid 16 including the cleaning concentrate can be re-circulated past the sensors 52 and 56.

This cleaning cycle continues under control of the controller 40 for a period of time determined by previous experiment or examination to be sufficient to properly clean the concentration sensor 52 and any optional sensors 56. The cooling and lubricating fluid 16 with the cleaner concentrate may remain in the monitoring assembly 30 and circulate at timed intervals, if desired, until a new measurement is required or it may be released. To release the fluid 16 containing the cleaner concentrate, the first solenoid valve 38 is activated to provide incoming fluid 16 and the second solenoid valve 58 is activated to allow egress of the fluid 16 present in the assembly 30. In this state, fluid readily flows through the bypass or cleaning loop 80 for a timed interval, removing the fluid 16 containing the concentrated cleaner. When that interval is complete, the normally open third solenoid valve 82 is activated and closes the bypass or cleaning loop 80. This action directs all incoming fluid to the pump 42. The electric motor 43 of the high pressure pump 42 is activated to assist drawing in the fluid 16 to be measured and filling the various components of the coolant and lubricant monitoring assembly 30 other than the bypass loop 80, thereby removing the fluid 16 containing the concentrated cleaner, allowing it to return to the main system. Alternatively, the normally closed second solenoid valve 58 is deactivated and at the same time, the normally closed fourth solenoid valve 86 is activated, thereby allowing the fluid 16 to flow to the waste container 88.

Figure 3:
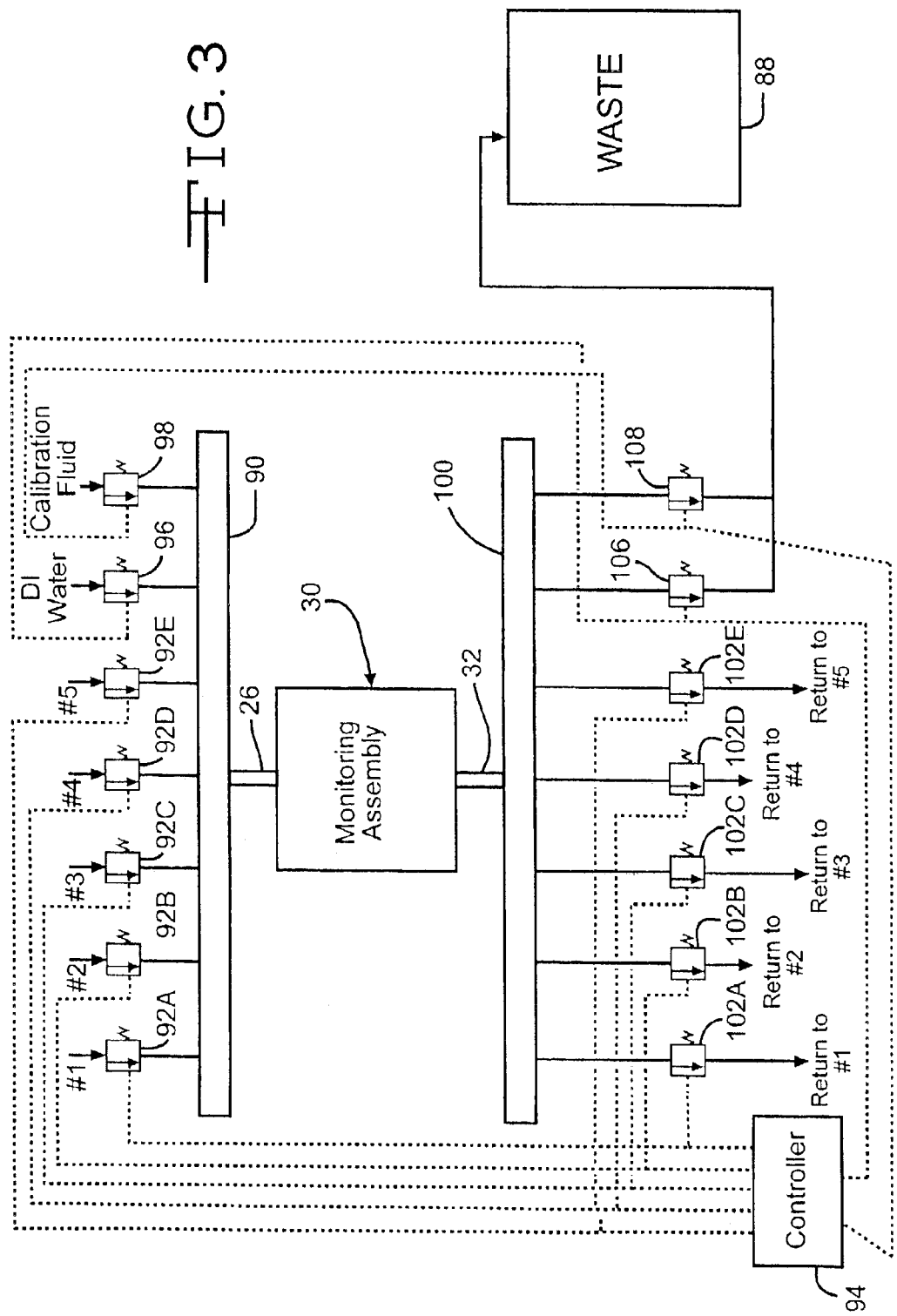
FIG. 3 is a diagrammatic view of input and output manifolds utilized in conjunction with the coolant and lubricant monitoring assembly according to the present invention.

Referring now to FIG. 3, the coolant and lubricant monitoring assembly 30 may also be utilized with inlet and outlet manifolds to permit it to both monitor fluids in several independent systems and be provided with various other task specific fluids. Accordingly, at the return and inlet line 26 providing fluid to the coolant and lubricant monitoring assembly 30 is an inlet manifold 90 having a plurality of independently operable inlet solenoid valves having their outlets in fluid communication therewith. Likewise, in fluid communication with the outlet line 32 is a second, outlet manifold 100 which has a plurality of independently operable outlet solenoid valves.

With regard to the inlet manifold 90, a plurality of solenoid operated valves 92A, 92B, 92C, 92D and 92E are provided with various fluids from various independent drilling, cutting, grinding and other manual and CNC machines having cooling or lubricating fluids 16 desired to be monitored. The solenoid valves 92A, 92B, 92C, 92D and 92E are controlled by a controller 40 (or an optional controller 94 which is linked to the controller 40 in order to achieve proper sequencing and system identification) and operate in concert but not simultaneously with a plurality of outlet valves 102A, 102B, 102C, 102D and 102E. That is, the controller 94 actuates the inlet valve 92A to receive fluid 16 and subsequently may operate the outlet valve 102A such that fluid 16 may be returned to the same system 1. Correspondingly, the valves 92A and 102A may be closed and the valves, for example, 92C and 102C may be opened such that cooling and lubricating fluid 16 from a third system is provided to the coolant and lubricant monitoring assembly 30 and returned thereto.

It should be understood that while five input valves 92A, 92B, 92C, 92D and 92E as well as a corresponding five outlet valves 102A, 102B, 102C, 102D and 102E are illustrated, the number five is exemplary only and more or fewer valves and associated systems may be readily accommodated and utilized with the coolant and lubricant monitoring assembly 30.

Additionally, cleaning fluid such as de-ionized water or calibration fluids may be provided to the assembly 30 through the inlet manifold 90 and removed through the outlet manifold 100. Specifically, an inlet solenoid valve 96 may be provided with de-ionized water from an appropriate source. The inlet solenoid valve 96 is operated to provide de-ionized water to the monitoring assembly 30. A first waste or outlet valve 106 may be appropriately activated to release the de-ionized water from the assembly 30 which travels to the waste vessel 88. Similarly, a calibration or other fluid may be provided to an inlet solenoid valve 98. The calibration fluid may be utilized in the coolant and lubricant monitoring assembly 30 to perform a calibration check on the various sensors 52 and 56 or achieve a desired operational or control function. As used herein calibration check means to utilize a standard reference or calibration fluid in the monitoring assembly 30 which, when read by one of the sensors 52 or 56, provides a current calibration signal or value to the controller 40 or other associated equipment. This current calibration signal can then be compared to a known, stored, reference value and the current accuracy of the sensor 52 or 56 can be determined. If the current signal or value differs from the stored reference value, an error compensation signal sufficient to compensate for the error can be generated and utilized to normalize or correct the output value of the sensors 52 and 56. The calibration fluid may then be released from the monitoring assembly 30 through a corresponding second waste or outlet valve 108 which provides the fluids to the waste vessel 88.

Figure 4:
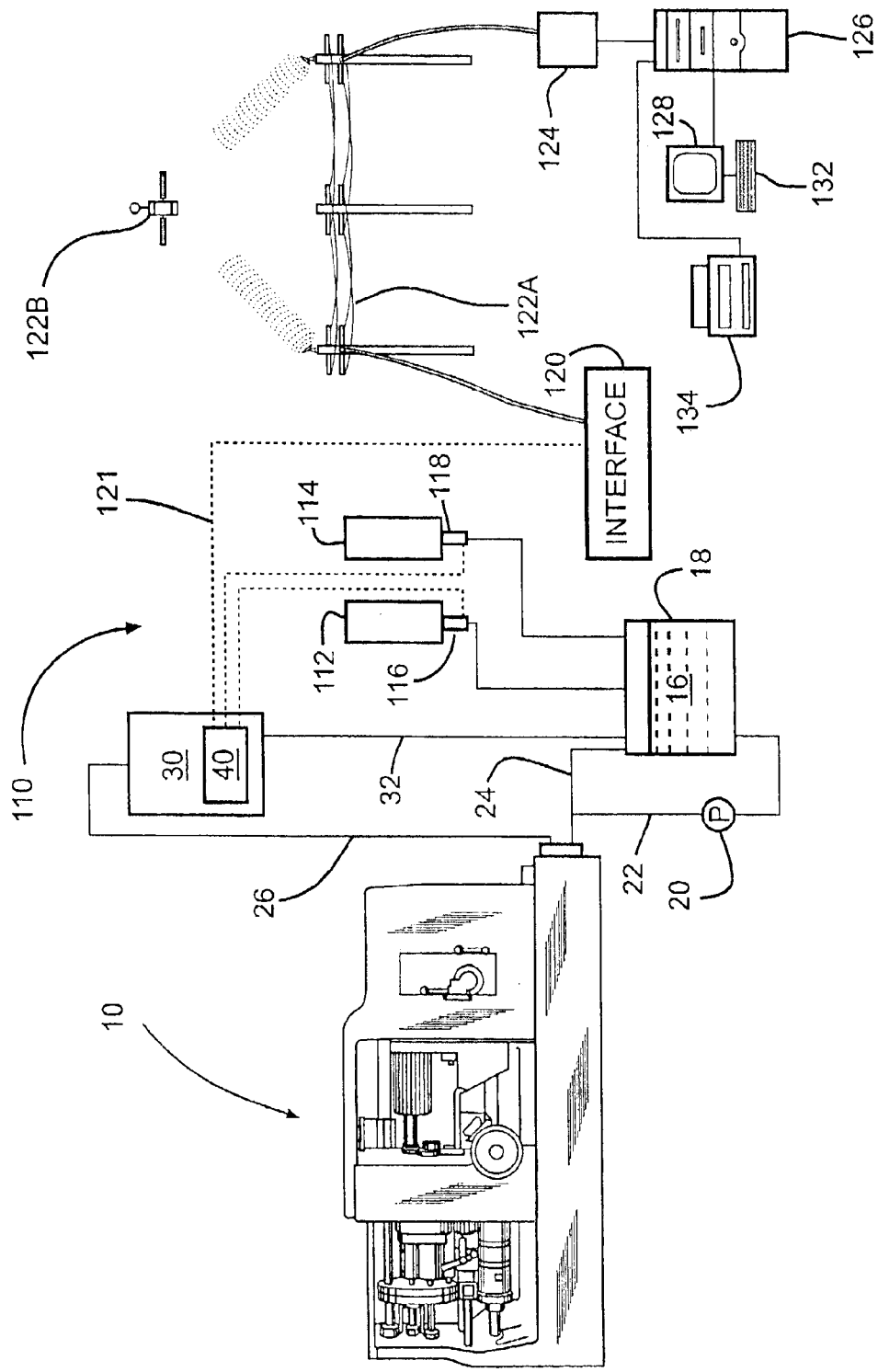
FIG. 4 is a diagrammatic view of a coolant and lubricant monitoring assembly according to the present invention located at a site remote from a monitoring site.

Referring now to FIG. 4, an installation having real time control and remote monitoring capability of at least one variable in a cooling and lubricating fluid system 110 is illustrated. Again, the system utilizes an automatic screw machine 10 or other device such as a computer numerical controlled (CNC) device, machining center, lathe, grinder, milling machine or similar cutting, forming, boring, drilling or shaping device including, in the cooling and lubricating fluid circuit the coolant and lubricant monitoring assembly 30 of the present invention, the sump 18 and the pump 20. The system 110 also includes supplies of one or more coolant or lubricant constituents contained within storage tanks or vessels 112 and 114. The storage vessels 112 and 114 may contain concentrated coolants, lubricants, pH adjusters or any other fluid or constituent of a cooling and lubricating fluid 16 which may be necessary to provide, augment or adjust the fluid characteristics. The vessels 112 and 114 preferably include electrically operated solenoid outlet valves 116 and 118, respectively, that are controlled by the controller 40 which receives signals from the various coolant and lubricant sensors 52 and 56, illustrated in FIG. 2.

A deficiency in some sensed characteristic or variable of the cooling and lubricating fluid 16 or other out of tolerance operating condition may be promptly and accurately corrected by activating one or both of the solenoid valves 116 and 118 to provide the necessary fluid(s) in the correct amount to correct the sensed deficiency. It should be understood that the foregoing description of two tanks or vessels 112 and 114 of constituents is illustrative only and that a single tank filled with a single constituent or a mixture of constituents or multiple (more than two) tanks with single constituents are within the purview of the present invention.

A first interface assembly 120 is coupled to the controller 40 by lines 121 and by land lines 122A such as telephone lines, internet connections, fiber optic lines or may be utilized in a wireless mode through microwave transmission or satellite transmission 122B to a second interface assembly 124 at a remote location. The second interface assembly 124 is preferably coupled to a computer 126 having a display device 128 such as a cathode ray tube or plasma display, a keyboard 132 for inputting data and a printer 134 and/or other electronic media or optical read/write storage device for providing a permanent record of operations and conditions.

So configured, data sensed by the sensors 52 and 56 of the coolant and lubricant monitoring assembly 30 is provided to the controller and interface assembly 120, transmitted to the interface assembly 124 and the computer 126. The data may then be stored therein or displayed on the display device 128 or printed out on the printer 134. Operators at the remote location can thus monitor one or many remote sites and operating conditions or events occurring at the remote locations and receive data or information in real time regarding operational parameters of the various systems. Moreover, permanent records of various fluid characteristics may be created by the printer 134 and/or other electronic media or optical storage device. Furthermore, a record of the corrective action taken in response to data collected may also be made.

It should be appreciated that the present system, particularly the coolant and lubricant monitoring assembly 30 may be used with all currently utilized cooling and/or lubricating fluids. That is, soluble oils which consist of oil, an emulsifier and are typically between 10% and 90% water; synthetic fluid in which no oil is utilized and semi-synthetic fluids wherein some oil is utilized are all suitable for use with the monitoring assembly 30. As noted previously, the concentrated cleaning fluid must therefore be selected to correspond from a solubility standpoint with the particular type of coolant and lubricating fluid 16 utilized in a specific system.

It is therefore intended that the foregoing detailed description be regarded as illustrative rather than limiting, and that it be understood that the following claims, including all equivalents, are intended to define the spirit and scope of this invention.

We claim:

1. An apparatus for monitoring a metal working parameter in a fluid system comprising, in combination, a fluid circuit, an inlet valve for controlling flow of a metal working fluid from such system into said circuit, a pump for circulating such fluid in said circuit, a refractometer for sensing a parameter of such fluid in said circuit, an outlet valve for controlling release of such fluid from said circuit, a source of a functional material, a metering device for injecting said functional material into said fluid circuit; and an inlet manifold having a plurality of fluid inlets and inlet valves and an outlet manifold having a plurality of outlet valves and fluid outlets.

2. The apparatus of claim 1 wherein said parameter is concentration of a constituent of said metal working fluid.

3. The apparatus of claim 1 wherein said functional material is a solvent of such fluid.

4. The apparatus of claim 1 wherein said functional material is selected from the group consisting of cleaning fluid, de-ionized water and calibration fluid.

5. The apparatus of claim 1 further including a controller for sequencing said valves, said pump and said metering device.

6. The apparatus of claim 1 further including a valve for establishing a recirculation path in said fluid circuit.

7. An apparatus for monitoring a parameter in a metal working fluid system comprising, in combination, a fluid circuit, an inlet valve for controlling flow of a metal working fluid from such system into said circuit, a pump for circulating fluid in said circuit, a refractometer for sensing a parameter of such fluid in said circuit, an outlet valve for controlling release of fluid from said circuit, a metering device for injecting a selected quantity of a functional material into said fluid circuit, a controller for sequencing operation of said valves, said pump and said metering device, and an inlet manifold having at least two fluid inlets and valves and an outlet manifold having at least two outlet valves and outlets.

8. The apparatus of claim 7 further including a valve for establishing a recirculation path in said fluid circuit.

9. The apparatus of claim 7 wherein said functional material is selected from the group consisting of a cleaning fluid, de-ionized water and a calibration fluid.

10. The apparatus of claim 7 wherein said parameter is concentration of such constituent of a metal working fluid.

11. The apparatus of claim 7 wherein said functional material is a solvent of such fluid.

12. A method of monitoring a parameter of a metal working fluid in a fluid system, comprising the steps of:

providing a first manifold having at least two inlets and corresponding inlet valves, providing a fluid circuit having a pump, providing a flow of a metal working fluid from said fluid system in said fluid circuit, exposing a refractometer to said metal working fluid to measure a fluid parameter, injecting a quantity of a functional material into said fluid circuit, circulating said fluid and said functional material in said fluid circuit, and providing a second manifold having at least two outlet valves.

13. The method of monitoring a parameter of a fluid of claim 12 wherein said parameter is concentration of constituent of said metal working fluid.

14. The method of monitoring a parameter of a fluid of claim 12 wherein said functional material is a solvent of such fluid.

15. The method of monitoring a parameter of a fluid of claim 12 wherein said functional material is selected from the group consisting of cleaning fluid, de-ionized water and calibration fluid or any other functional material required to accomplish the cleaning and/or calibration check function.

16. The method of monitoring a parameter of a fluid of claim 12 further including providing a valve for establishing a recirculation path in said fluid circuit and recirculating fluid in said circuit.

17. An apparatus for monitoring a parameter in a fluid system comprising, in combination, a fluid circuit, an inlet valve for controlling flow of a fluid from such system into said circuit, a pump for circulating such fluid in said circuit, at least one sensor for sensing a parameter of such fluid in said circuit, an outlet valve for controlling release of such fluid from said circuit, a source of a functional material, and a metering device for injecting said functional material into said fluid circuit; and an inlet manifold having a plurality of fluid inlets and inlet valves and an outlet manifold having a plurality of outlet valves.

18. The apparatus for monitoring a parameter in a fluid system of claim 17 wherein said at least one sensor is a refractometer.

19. The apparatus for monitoring a parameter in a fluid system of claim 17 wherein said inlets are coupled to sources of distinct fluids and said outlets are coupled to one of said sources or a waste receiver.

* * * * *